US010787688B2

(12) United States Patent
Haas et al.

(10) Patent No.: US 10,787,688 B2
(45) Date of Patent: Sep. 29, 2020

(54) MULTI-STAGE SYNTHESIS METHOD WITH SYNTHESIS GAS

(71) Applicant: Evonik Operations GmbH, Essen (DE)

(72) Inventors: Thomas Haas, Muenster (DE); Eva Maria Wittmann, Traunreut (DE)

(73) Assignee: Evonik Operations GmbH, Essen (DE)

( * ) Notice: Subject to any disclaimer, the term of this patent is extended or adjusted under 35 U.S.C. 154(b) by 29 days.

(21) Appl. No.: 14/400,379

(22) PCT Filed: May 8, 2013

(86) PCT No.: PCT/EP2013/059608
§ 371 (c)(1),
(2) Date: Nov. 11, 2014

(87) PCT Pub. No.: WO2013/167663
PCT Pub. Date: Nov. 14, 2013

(65) Prior Publication Data
US 2015/0125912 A1 May 7, 2015

(30) Foreign Application Priority Data
May 11, 2012 (DE) .................. 10 2012 207 921

(51) Int. Cl.
| C12P 7/64 | (2006.01) |
| C12P 7/40 | (2006.01) |
| C12P 7/42 | (2006.01) |
| C12P 7/62 | (2006.01) |
| C12P 7/24 | (2006.01) |
| C12P 7/46 | (2006.01) |
| C12P 7/54 | (2006.01) |
| C12P 7/06 | (2006.01) |
| C12P 7/02 | (2006.01) |

(52) U.S. Cl.
CPC ............... *C12P 7/6409* (2013.01); *C12P 7/02* (2013.01); *C12P 7/065* (2013.01); *C12P 7/24* (2013.01); *C12P 7/40* (2013.01); *C12P 7/42* (2013.01); *C12P 7/46* (2013.01); *C12P 7/54* (2013.01); *C12P 7/62* (2013.01); *C12P 7/6436* (2013.01); *Y02E 50/17* (2013.01)

(58) Field of Classification Search
CPC .................................. C12P 7/54; Y02E 50/17
See application file for complete search history.

(56) References Cited

U.S. PATENT DOCUMENTS

| 4,720,457 | A | 1/1988 | Armstrong et al. |
| 7,923,225 | B2 | 4/2011 | Mueller et al. |
| 8,110,670 | B2 * | 2/2012 | Hu ........................ C10L 1/02 536/23.2 |
| 8,349,596 | B2 | 1/2013 | Mueller et al. |
| 8,703,451 | B2 | 4/2014 | Haas et al. |
| 2003/0212298 | A1 | 11/2003 | Brasse et al. |
| 2009/0203098 | A1 * | 8/2009 | Verser ................ C07C 29/147 435/160 |
| 2010/0105115 | A1 | 4/2010 | Simpson et al. |
| 2010/0324257 | A1 | 12/2010 | Karau et al. |
| 2011/0118433 | A1 | 5/2011 | Pötter et al. |
| 2011/0118504 | A1 | 5/2011 | Haas et al. |
| 2011/0171702 | A1 | 7/2011 | Reinecke et al. |
| 2011/0189742 | A1 | 8/2011 | Haas et al. |
| 2012/0034665 | A1 | 2/2012 | Haas et al. |
| 2013/0052700 | A1 | 2/2013 | Poetter et al. |
| 2013/0164797 | A1 | 6/2013 | Gielen et al. |
| 2013/0183725 | A1 | 7/2013 | Poetter et al. |
| 2014/0120587 | A1 | 5/2014 | Haas et al. |
| 2014/0178948 | A1 | 6/2014 | Schaffer et al. |
| 2014/0186905 | A1 | 7/2014 | Schaffer et al. |
| 2014/0242646 | A1 | 8/2014 | Pötter et al. |
| 2014/0256904 | A1 | 9/2014 | Schaffer et al. |
| 2014/0308717 | A1 | 10/2014 | Haas et al. |

FOREIGN PATENT DOCUMENTS

| CN | 101918567 A | 12/2010 |
| CN | 102203267 A | 9/2011 |
| WO | 2008/115080 A1 | 9/2008 |
| WO | WO 2008/148640 A1 | 12/2008 |
| WO | WO 2009/030654 A1 | 3/2009 |
| WO | WO 2009/058028 A1 | 5/2009 |

(Continued)

OTHER PUBLICATIONS

U.S. Appl. No. 14/435,339, filed Apr. 13, 2015, Engel, et al.
U.S. Appl. No. 14/425,180, filed Mar. 2, 2015, Ortelt, et al.
U.S. Appl. No. 14/763,378, filed Jul. 24, 2015, Haas, et al.
International Search Report dated Dec. 5, 2013 in PCT/EP2013/059608 filed May 8, 2013.
U.S. Appl. No. 14/363,178, filed Jun. 5, 2014, Haas, et al.
U.S. Appl. No. 14/390,133, filed Oct. 2, 2014, Hennemann, et al.
U.S. Appl. No. 14/380,483, filed Aug. 22, 2014, Schiemann, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.

(Continued)

*Primary Examiner* — Taeyoon Kim
*Assistant Examiner* — Tiffany M Gough
(74) *Attorney, Agent, or Firm* — Oblon, McClelland, Maier & Neustadt, L.L.P.

(57) ABSTRACT

The invention provides a process for the preparation of hydrocarbons substituted with at least one group containing at least one oxygen atom, comprising the process steps
A) reaction of a carbon source comprising at least one selected from $CO_2$ and CO to give acetate and/or ethanol with a first microorganism,
B) separating off of the acetate from the first microorganism,
C) reaction of the acetate to give a hydrocarbon substituted with at least one group containing at least one oxygen atom with a second microorganism and optionally
D) purification of the hydrocarbon substituted with at least one group containing at least one oxygen atom.

20 Claims, 1 Drawing Sheet
Specification includes a Sequence Listing.

(56) References Cited

FOREIGN PATENT DOCUMENTS

| WO | WO 2009/077461 | A1 | 6/2009 |
|----|----|----|----|
| WO | WO 2009/078973 | A2 | 6/2009 |
| WO | WO 2009/156214 | A1 | 12/2009 |
| WO | 2010/000506 | A2 | 1/2010 |
| WO | 2010/000506 | A3 | 1/2010 |
| WO | WO 2010/006834 | A2 | 1/2010 |
| WO | WO 2010/042664 | A2 | 4/2010 |
| WO | WO 2010/127318 | A2 | 11/2010 |
| WO | WO 2011/127409 | A2 | 10/2011 |
| WO | WO 2011/131420 | A1 | 10/2011 |
| WO | WO 2011/157573 | A2 | 12/2011 |
| WO | WO 2012/171666 | A1 | 12/2012 |
| WO | WO 2013/011018 | A1 | 1/2013 |
| WO | 2013/024111 | A1 | 2/2013 |
| WO | WO 2013/020839 | A1 | 2/2013 |
| WO | WO 2013/024114 | A2 | 2/2013 |
| WO | 2013/083374 | A1 | 6/2013 |
| WO | WO 2013/083412 | A1 | 6/2013 |
| WO | WO 2013/092426 | A1 | 6/2013 |
| WO | WO 2013/110557 | A1 | 8/2013 |
| WO | WO 2013/124401 | A1 | 8/2013 |
| WO | WO 2013/135650 | A1 | 9/2013 |
| WO | WO 2013/149864 | A1 | 10/2013 |
| WO | WO 2013/156454 | A1 | 10/2013 |
| WO | WO 2013/167663 | A2 | 11/2013 |
| WO | WO 2013/186340 | A1 | 12/2013 |
| WO | WO 2014/079683 | A1 | 5/2014 |
| WO | WO 2014/114505 | A1 | 7/2014 |
| WO | WO 2014/122005 | A1 | 8/2014 |

OTHER PUBLICATIONS

U.S. Appl. No. 14/384,301, filed Sep. 10, 2014, Schaffer, et al.
U.S. Appl. No. 14/395,666, filed Oct. 20, 2014, Haas, et al.
U.S. Appl. No. 14/405,050, filed Dec. 2, 2014, Haas, et al.
Combined Chinese Office Action and Search Report dated Aug. 26, 2016 in Patent Application No. 201380024696.5 (with English translation).
Office Action dated Sep. 25, 2019 in Korean Patent Application No. 10-2014-7031243 (with English translation).

* cited by examiner

SEQUENCE LISTING

<160> NUMBER OF SEQ ID NOS: 2

<210> SEQ ID NO 1
<211> LENGTH: 1143
<212> TYPE: DNA
<213> ORGANISM: Artificial Sequence
<220> FEATURE:
<223> OTHER INFORMATION: codon optimized gene

<400> SEQUENCE: 1

| | | | | | |
|---|---|---|---|---|---|
| gcggccgcaa | attcagtaag | cagaaagtca | aaagcctccg | accggaggct | tttgactatt | 60 |
| aggaaacgct | gttgccatta | gacgtcttgc | cggtgctaat | agcaccattc | gcacctgcat | 120 |
| tttcggacg | ccactcggtt | gcaccattga | cgattgcagt | accatcctcc | agacgcagca | 180 |
| ggtgttgata | ttggctacgc | acaccaactt | tggacgggtc | catcgccgtc | acgctttcca | 240 |
| aaacgctgtc | acggccgcac | tcgcgacgat | attccagagc | caggctgcac | agctcctgcg | 300 |
| tttccaggac | ctcggtcggc | atgctctcca | gaatccagcc | aatgtatttg | acgttgctga | 360 |
| catgttgatt | cacatccaga | tcgttccagc | ctggggtcaa | gccttttgg | atgctgtcac | 420 |
| cggtcttaac | cttgaactta | tggaccttca | gatcgctatc | ctcgataacc | ggagagtcaa | 480 |
| cgaacagagg | gacgatttcc | tgatgcacct | cgtacggcag | cttgctcagg | cgacgagttt | 540 |
| tctgattcat | catggcatac | gcgctggtcg | cacgcaccag | gatttcgccc | gtattgcaat | 600 |
| cgctaatcag | ccagtcgcga | cccataccaa | tcttacccag | acggctgaaa | cgcgtgttaa | 660 |
| tctcaacggt | gtcaccccag | gccgggtaac | ggttaacttt | gatctgcatc | ttaatcacca | 720 |
| cccaaatcaa | atcacgctta | cacatctcca | gggtgcgacc | gaaaccatcc | aacaggatac | 780 |
| cggtagattt | acagtggttc | aagctggttt | cctgcaggtg | gttcatcagg | gtttcgatgc | 840 |
| tcgcggtacg | atccgtgcca | atctcgtagc | tgcggatgct | aaaggattga | cgaaacacca | 900 |
| ggccgtcctg | gaccgtgctt | tccagaccaa | acgagtctac | cagcatgtcc | gggcgtttgg | 960 |
| atttgcggtc | gtgcatatgt | tttacctcct | gttaaacaaa | attatttcta | gagggaaacc | 1020 |
| gttgtggaat | tgtgagcgct | cacaattcca | catccacaca | ttatacgagc | cgatgattaa | 1080 |
| ttgtcaacag | cgtcgatcac | tgtgcatgaa | gctcgtaatt | gttatccgct | cacaattgga | 1140 |
| tcc | | | | | | 1143 |

<210> SEQ ID NO 2
<211> LENGTH: 4985
<212> TYPE: DNA
<213> ORGANISM: Artificial Sequence
<220> FEATURE:
<223> OTHER INFORMATION: vector

<400> SEQUENCE: 2

| | | | | | |
|---|---|---|---|---|---|
| accaatgctt | aatcagtgag | gcacctatct | cagcgatctg | tctatttcgt | tcatccatag | 60 |
| ttgcctgact | ccccgtcgtg | tagataacta | cgatacggga | gggcttacca | tctggcccca | 120 |
| gcgctgcgat | gataccgcga | gaaccacgct | caccggctcc | ggatttatca | gcaataaacc | 180 |
| agccagccgg | aagggccgag | cgcagaagtg | gtcctgcaac | tttatccgcc | tccatccagt | 240 |
| ctattaattg | ttgccgggaa | gctagagtaa | gtagttcgcc | agttaatagt | ttgcgcaacg | 300 |
| ttgttgccat | cgctacaggc | atcgtggtgt | cacgctcgtc | gtttggtatg | gcttcattca | 360 |
| gctccggttc | ccaacgatca | aggcgagtta | catgatcccc | catgttgtgc | aaaaaagcgg | 420 |
| ttagctcctt | cggtcctccg | atcgttgtca | gaagtaagtt | ggccgcagtg | ttatcactca | 480 |
| tggttatggc | agcactgcat | aattctctta | ctgtcatgcc | atccgtaaga | tgcttttctg | 540 |

```
tgactggtga gtactcaacc aagtcattct gagaatagtg tatgcggcga ccgagttgct    600
cttgcccggc gtcaatacgg gataataccg cgccacatag cagaacttta aaagtgctca    660
tcattggaaa acgttcttcg gggcgaaaac tctcaaggat cttaccgctg ttgagatcca    720
gttcgatgta acccactcgt gcacccaact gatcttcagc atcttttact ttcaccagcg    780
tttctgggtg agcaaaaaca ggaaggcaaa atgccgcaaa aaagggaata agggcgacac    840
ggaaatgttg aatactcata ttcttccttt tcaatatta ttgaagcatt tatcaggggtt    900 attgtctcat gagcggatac atatttgaat gtatttagaa aaataaacaa ataggggtca    960
gtgttacaac caattaacca attctgaaca ttatcgcgag cccatttata cctgaatatg   1020
gctcataaca ccccttgttt gcctggcggc agtagcgcgg tggtcccacc tgaccccatg   1080
ccgaactcag aagtgaaacg ccgtagcgcc gatggtagtg tggggactcc ccatgcgaga   1140
gtagggaact gccaggcatc aaataaaacg aaaggctcag tcgaaagact gggcctttcg   1200
cccgggctaa ttatggggtg tcgcccttat tcgactctat agtgaagttc ctattctcta   1260
gaaagtatag gaacttctga agtggggggcg ccgcaaatt cagtaagcag aaagtcaaaa   1320
gcctccgacc ggaggctttt gactattagg aaacgctgtt gccattagac gtcttgccgg   1380
tgctaatagc accattcgca cctgcatttt tcggacgcca ctcggttgca ccattgacga   1440
ttgcagtacc atcctccaga cgcagcaggt gttgatattg gctacgcaca ccaactttgg   1500
acgggtccat cgccgtcacg cttttccaaaa cgctgtcacg gccgcactcg cgacgatatt   1560
ccagagccag gctgcacagc tcctgcgttt ccaggacctc ggtcggcatg ctctccagaa   1620
tccagccaat gtatttgacg ttgctgacat gttgattcac atccagatcg ttccagcctg   1680
gggtcaagcc ttttttggatg ctgtcaccgg tcttaacctt gaacttatgg accttcagat   1740
cgctatcctc gataaccgga gagtcaacga acagagggac gatttcctga tgcacctcgt   1800
acggcagctt gctcaggcga cgagttttct gattcatcat ggcatacgcg ctggtcgcac   1860
gcaccaggat ttcgcccgta ttgcaatcgc taatcagcca gtcgcgaccc ataccaatct   1920
tacccagacg gctgaaacgc gtgttaatct caacggtgtc accccaggcc gggtaacggt   1980
taactttgat ctgcatctta atcaccaccc aaatcaaatc acgcttacac atctccaggg   2040
tgcgaccgaa accatccaac aggataccgg tagatttaca gtggttcaag ctggtttcct   2100
gcaggtggtt catcagggtt tcgatgctcg cggtacgatc cgtgccaatc tcgtagctgc   2160
ggatgctaaa ggattgacga acaccaggc cgtcctggac cgtgctttcc agaccaaacg   2220
agtctaccag catgtccggg cgtttggatt tgcggtcgtg catatgtttt acctcctgtt   2280
aaacaaaatt atttctagag ggaaaccgtt gtggaattgt gagcgctcac aattccacat   2340
ccacacatta tacgagccga tgattaattg tcaacagcgt cgatcactgt gcatgaagct   2400
cgtaattgtt atccgctcac aattggatcc aaaatgaagg gaagttccta tactttctag   2460
agaataggaa cttctatagg gagtcgaata agggcgacac aaaaggtatt ctaaatgcat   2520
aataaatact gataacatct tatagtttgt attatatttt gtattatcgt tgacatgtat   2580
aattttgata tcaaaaactg attttccctt tattattttc gagatttatt ttcttaattc   2640
tctttaacaa actagaaata ttgtatatac aaaaaatcat aaataataga tgaatagttt   2700
aattataggt gttcatcaat cgaaaaagca acgtatctta tttaaagtgc gttgcttttt   2760 tctcattttat aaggttaaat aattctcata tatcaagcaa agtgacaggc gcccttaaat   2820
attctgacaa atgctctttc cctaaactcc ccccataaaa aaacccgccg aagcgggttt   2880
```

-continued

```
ttacgttatt tgcggattaa cgattactcg ttatcagaac cgcccaggat gcctggcagt    2940
tccctactct cgccgctgcg ctcggtcgtt cggctgcggg acctcagcgc tagcggagtg    3000
tatactggct tactatgttg gcactgatga gggtgtcagt gaagtgcttc atgtggcagg    3060
agaaaaaagg ctgcaccggt gcgtcagcag aatatgtgat acaggatata ttccgcttcc    3120
tcgctcactg actcgctacg ctcggtcgtt cgactgcggc gagcggaaat ggcttacgaa    3180
cggggcggag atttcctgga agatgccagg aagatactta acaggaagt gagagggccg     3240
cggcaaagcc gttttccat aggctccgcc ccctgacaa gcatcacgaa atctgacgct      3300
caaatcagtg gtggcgaaac ccgacaggac tataaagata ccaggcgttt ccccctggcg    3360
gctccctcgt gcgctctcct gttcctgcct ttcggtttac cggtgtcatt ccgctgttat    3420
ggccgcgttt gtctcattcc acgcctgaca ctcagttccg ggtaggcagt tcgctccaag    3480
ctggactgta tgcacgaacc ccccgttcag tccgaccgct gcgccttatc cggtaactat    3540
cgtcttgagt ccaacccgga aagacatgca aaagcaccac tggcagcagc cactggtaat    3600
tgatttagag gagttagtct tgaagtcatg cgccggttaa ggctaaactg aaaggacaag    3660
ttttggtgac tgcgctcctc caagccagtt acctcggttc aaagagttgg tagctcagag    3720
aaccttcgaa aaaccgccct gcaaggcggt ttttcgttt tcagagcaag agattacgcg     3780
cagaccaaaa cgatctcaag aagatcatct tattaatcac tgcccgcttt ccagtcggga    3840
aacctgtcgt gccagctgca ttaatgaatc ggccaacgcg cggggagagg cggtttgcgt    3900
attgggcgcc agggtggttt ttcttttcac cagtgagact ggcaacagct gattgccctt    3960
caccgcctgg ccctgagaga gttgcagcaa gcggtccacg ctggtttgcc ccagcaggcg    4020
aaaatcctgt ttgatggtgg ttaacggcgg gatataacat gagctatctt cggtatcgtc    4080
gtatcccact accgagatat ccgcaccaac gcgcagcccg gactcggtaa tggcgcgcat    4140
tgcgcccagc gccatctgat cgttggcaac cagcatcgca gtgggaacga tgccctcatt    4200
cagcatttgc atggtttgtt gaaaaccgga catggcactc cagtcgcctt cccgttccgc    4260
tatcggctga atttgattgc gagtgagata tttatgccag ccagccagac gcagacgcgc    4320
cgagacagaa cttaatgggc ccgctaacag cgcgatttgc tggtgaccca atgcgaccag    4380
atgctccacg cccagtcgcg taccgtcctc atgggagaaa ataatactgt tgatgggtgt    4440
ctggtcagag acatcaagaa ataacgccgg aacattagtg caggcagctt ccacagcaat    4500
ggcatcctgg tcatccagcg gatagttaat gatcagccca ctgacgcgtt gcgcgagaag    4560
attgtgcacc gccgctttac aggcttcgac gccgcttcgt tctaccatcg acaccaccac    4620
gctggcaccc agttgatcgg cgcgagattt aatcgccgcg acaatttgcg acggcgcgtg    4680
cagggccaga ctggaggtgg caacgccaat cagcaacgac tgtttgcccg ccagttgttg    4740
tgccacgcgg ttgggaatgt aattcagctc cgccatcgcc gcttccactt tttcccgcgt    4800
tttcgcagaa acgtggctgg cctggttcac cacgcgggaa acggtctgat aagagacacc    4860
ggcatactct gcgacatcgt ataacgttac tggtttcata ttcaccaccc tgaattgact    4920
ctcttccggg cgctatcatg ccataccgcg aaaggttttg cgccattcga tggcgcgccg    4980
ctttt                                                                4985
```

MULTI-STAGE SYNTHESIS METHOD WITH SYNTHESIS GAS

FIELD OF THE INVENTION

The invention relates to a process for the preparation of hydrocarbons substituted with at least one group containing at least one oxygen atom, comprising the process steps
A) reaction of a carbon source comprising at least one selected from $CO_2$ and CO to give acetate and/or ethanol with a first microorganism,
B) separating off of the acetate and/or ethanol from the first microorganism,
C) reaction of the acetate and/or ethanol to give a hydrocarbon substituted with at least one group containing at least one oxygen atom with a second microorganism and optionally
D) purification of the hydrocarbon substituted with at least one group containing at least one oxygen atom.

PRIOR ART

The use of $CO_2$ as a carbon source for the synthesis of organic compounds in microbiological processes is often described in the literature.

As a rule, the prior art attempts to map two supplementary metabolic pathways from different organisms in a recombinant cell, with the help of which the organic substance can then be synthesized.

Here, the problem arises that the different organisms whose properties are to be brought together constitute very highly specialized organisms from niches, and it is therefore difficult to be able to combine the sum of all of the advantages associated therewith in one cell.

Additionally, a lack of genetic accessibility of these organisms hinders the desired manipulation. Alternative processes for using $CO_2$ as a carbon source influence a microorganism which is known for being able to fix $CO_2$ through a certain selection of the fermentation parameters, such that said microorganism synthesizes to an increased extent a desired, simple organic substance, such as, for example, ethanol, n-butanol or 2,3-butanediol.

WO200068407 describes the use of acetogenic bacteria for producing ethanol, and WO2012024522 describes the use of acetogenic bacteria for producing butanediol.

All of the described processes have the disadvantage that the yields are low and that the use of a single cell type does not allow any flexibility with the fermentation conditions.

It was an object of the invention to provide a process which was able to overcome at least the disadvantage of the prior art.

DESCRIPTION OF THE INVENTION

Surprisingly, it has been found that the multistage process described below with a separation of acetate production from $CO_2$ and/or CO from the acetate further processing was able to overcome prior art disadvantages in the simplest of manners.

The present invention therefore provides a process as described in Claim 1 and the other independent claims.

One advantage of the present invention is that $CO_2$/CO mixtures are an essentially more favourable raw material which can moreover be produced from various sources, such as natural gas and biogas, coal, oil, and also plant residues.

A further advantage of the process according to the invention is the high carbon yield. This is made possible by the recycling of formed $CO_2$. This is because the $CO_2$ can be reacted in the first stage again to give acetic acid.

A further advantage lies in the greater flexibility as regards the fermentation conditions used since for the actual production in process step C) according to the invention a different organism is used than for the carbon fixing in the acetate.

A yet further advantage of the present invention is that by using acetate and/or ethanol, in particular acetate, as carbon source in process step C), different product compositions can arise than if a sugar is used in process step C).

The present invention provides a process for the preparation of hydrocarbons substituted with at least one group containing at least one oxygen atom, comprising the process steps
A) reaction of a carbon source comprising at least one selected from $CO_2$ and CO to give acetate and/or ethanol, in particular acetate, with a first microorganism,
B) separating off of the acetate and/or ethanol, in particular acetate, from the first microorganism,
C) reaction of the acetate and/or ethanol, in particular acetate, to give a hydrocarbon substituted with at least one group containing at least one oxygen atom with a second microorganism and optionally
D) purification of the hydrocarbon substituted with at least one group containing at least one oxygen atom, preferably with at least 3, in particular at least 4 carbon atoms.

In connection with the present invention, the term "acetate" is to be understood as meaning both acetic acid and also its salts; this arises automatically since the microorganisms work in aqueous medium, and there is thus always an equilibrium between salt and acid.

In connection with the present invention, the term "second microorganism" is to be understood as meaning a different one to the "first microorganism" from process step A).

Unless stated otherwise, all of the stated percentages (%) are percent by mass.

In the process according to the invention, in process step A) acetate and/or ethanol is formed by a first microorganism from a carbon source comprising carbon dioxide and/or carbon monoxide; this wording includes the case that the acetate and/or ethanol is formed at least partially from carbon dioxide and/or carbon monoxide.

With regard to the source of the substrates carbon dioxide and/or carbon monoxide, it is evident that many possible sources exist for the provision of CO and/or $CO_2$ as carbon source. It is clear that in practice the carbon source of the present invention that can be used is any gas or any gas mixture which is able to supply microorganisms with sufficient amounts of carbon to enable them to form acetate and/or ethanol.

In the process according to the invention, it is preferred that the carbon source is provided by waste gases such as, for example, synthesis gas, flue gas, petroleum refinery waste gases, gases formed as a result of yeast fermentation or clostridial fermentation, waste gases from the gasification of cellulose-containing materials or of carbon gasification.

In this connection, it is particularly preferred that at least some of the carbon dioxide and/or carbon monoxide constitutes a by-product of process step C) of the process according to the invention. This has the technical effect that the carbon yield is 100% over the entire process. These waste gases do not necessarily have to be formed as secondary phenomena of different processes, but may be produced specially for use in the process according to the invention.

In a preferred embodiment of the process according to the invention, the carbon source is synthesis gas.

Synthesis gas can be provided e.g. from the by-product of carbon gasification. The microorganism consequently converts a substance that is a waste product into a valuable raw material.

Alternatively, synthesis gas can be provided by the gasification of widely available, cost-effective agricultural raw materials for the process according to the invention.

There are numerous examples of raw materials which can be converted into synthesis gas since almost all forms of vegetation can be utilized for this purpose. Preferred raw materials are selected from the group comprising perennial grasses such as *Miscanthus sinensis*, cereal residues, processing waste such as sawdust.

In general, synthesis gas is obtained in a gasification apparatus from dried biomass, primarily by pyrolysis, partial oxidation and steam reformation, the primary products being $CO$, $H_2$ and $CO_2$.

Normally, some of the product gas is processed in order to optimize product yields and to avoid tar formation. The cracking of the undesired tar into synthesis gas and CO can be carried out with the use of lime and/or dolomite. These processes are described in detail in e.g. Reed, 1981 (Reed, T. B., 1981, Biomass gasification: principles and technology, Noves Data Corporation, Park Ridge, N.J.)

It is also possible to use mixtures of different sources as the carbon source.

In general, it is preferred in the process according to the invention that the carbon source in process step A) comprises at least 50% by weight, preferably at least 70% by weight, particularly preferably at least 90% by weight, of $CO_2$ and/or CO, where the % by weight refer to all of the carbon sources which are available to the microorganism in process step A).

In process step A), preferably a reducing agent, preferably hydrogen is conveyed together with the carbon dioxide and/or carbon monoxide to the reaction.

Consequently, a process that is preferred according to the invention is characterized in that the carbon source in process step A) comprises synthesis gas, in particular consists of synthesis gas.

Microorganisms which convert $CO_2$ and/or CO to acetate and/or ethanol, in particular acetate, as well as suitable processes and process conditions which can be used in process step A) have been known for a long time. Such processes are described for example in WO9800558, WO2000014052, WO2010115054 in Demler et al. *Reaction engineering analysis of hydrogenotrophic production of acetic acid by Acetobacterium woodii*. Biotechnol Bioeng. 2011 February; 108(2): 470-4, in Younesia et al. *Ethanol and acetate production from synthesis gas via fermentation processes using anaerobic bacterium, Clostridium ljungdahlii*. Biochemical Engineering Journal, Volume 27, Issue 2, pages 110 119, in Morinaga et al. *The production of acetic acid from carbon dioxide and hydrogen by an anaerobic bacterium*. Journal of Biotechnology, Volume 14, Issue 2, pages 187-194, in Li *Production of acetic acid from synthesis gas with mixed acetogenic microorganisms*, ISSN 0493644938, in Schmidt et al. *Production of acetic acid from hydrogen and carbon dioxide by clostridium species ATCC 2979*. Chemical Engineering Communications, 45:1-6, 61-73, in Sim et al. *Optimization of acetic acid production from synthesis gas by chemolithotrophic bacterium— Clostridium aceticum using a statistical approach*. Bioresour Technol. 2008 May; 99(8):2724-35, in Vega et al. *Study of gaseous substrate fermentations CO conversion to acetate* 1 *Batch culture* and 2 *continuous culture*. Biotechnology and Bioengineering Volume 34, Issue 6, pages 774 and 785, September 1989, in Cotter et al. *Ethanol and acetate production by Clostridium ljungdahlii and Clostridium autoethanogenum using resting cells*. Bioprocess and Biosystems Engineering (2009), 32(3), 369-380 and in Andreesen et al. *Fermentation of glucose, fructose, and xylose by Clostridium thermoaceticum. Effect of metals on growth yield, enzymes, and the synthesis of acetate from carbon dioxide*. Journal of Bacteriology (1973), 114(2), 743-51.

The person skilled in the art is offered from this a large number of feasible options for designing process step A) which all function well.

Of particular suitability in this connection are acetogenic bacteria. The group of acetogenic bacteria belongs to anaerobic prokaryotes which can utilize $CO_2$ as terminal electron acceptor and in so doing form acetate and/or ethanol. Currently, 21 different genera are included among the acetogens (Drake et al., 2006), of which some are also clostridia (Drake & Küsel, 2005). They are able to utilize carbon dioxide and also carbon monoxide as carbon and hydrogen as energy source (Wood, 1991). In addition, alcohols, aldehydes, carboxylic acids, and numerous hexoses can also be utilized as carbon source (Drake et al., 2004). The reductive metabolic pathway which leads to the formation of acetate is referred to as acetyl-CoA pathway or Wood-Ljungdahl pathway.

Consequently, it is preferred that in process step A) of the process according to the invention, an acetogenic bacterium is used as the first microorganism. Particular preference is given to using acetogenic bacteria selected from the group comprising *Clostridium autothenogenum* DSMZ 19630, *Clostridium ragsdahlei* ATCC no. BAA-622, *Clostridium autoethanogenum*, *Moorella* sp HUC22-1, *Moorella thermoaceticum*, *Moorella thermoautotrophica*, *Rumicoccus productus*, *Acetoanaerobum*, *Oxobacter pfennigii*, *Methanosarcina barkeri*, *Methanosarcina acetivorans*, *Carboxydothermus*, *Desulphotomaculum kutznetsovii*, *Pyrococcus*, *Peptostreptococcus*, *Butyribacterium methylotrophicum* ATCC 33266, *Clostridium formicoaceticum*, *Clostridium butyricum*, *Laktobacillus delbrukii*, *Propionibacterium acidoprprionici*, *Proprionispera arboris*, *Anaerobierspirillum succiniproducens*, *Bacterioides amylophilus*, *Becterioides ruminicola*, *Thermoanaerobacter kivui*, *Acetobacterium Acetoanaerobium notera*, *Clostridium aceticum*, *Butyribacterium methylotrophicum*, *Moorella thermoacetica*, *Eubacterium limosum*, *Peptostreptococcus productus*, *Clostridium ljungdahlii*, *Clostridium* ATCC 29797 and *Clostridium carboxidivorans*, in particular ATCC BAA-624. A particularly suitable bacterium is *Clostridium carboxidivorans*, in particular those strains such as "P7" and "P11". Such cells are described for example in US 2007/0275447 and US 2008/0057554.

The further particularly suitable bacterium is *Clostridium ljungdahlii*, in particular strains selected from the group comprising *Clostridium ljungdahlii* PETC, *Clostridium ljungdahlii* ERI2, *Clostridium ljungdahlii* COI and *Clostridium ljungdahlii* O-52, these are described in WO 98/00558 and WO 00/68407, and also ATCC 49587, ATCC 55988 and ATCC 55989.

In a particularly preferred embodiment of the process according to the invention, in process step A) ethanol is formed and the microorganism used is *Alkalibaculum bacchi* ATCC BAA-1772, *Moorella* sp. HUC22-1, *Clostridium ljungdahlii*, *Clostridium ragsdahlei*, or *Clostridium autoethanogenum*. Corresponding instructions for carrying out process step A) can be found for example in Saxena et al. *Effect of trace metals on ethanol production from synthesis gas by the ethanologenic acetogen Clostridium ragsdalei*. Journal of Industrial Microbiology & Biotechnology Volume 38, Number 4 (2011), 513-521, Younesi et al. *Ethanol and acetate production from synthesis gas via fermentation processes using anaerobic bacterium Clostridium ljungdahlii*. Biochemical Engineering Journal Volume 27, Issue 2, 15 Dec. 2005, pages 110-119, Sakai et al. *Ethanol production from H2 and CO2 by a newly isolated thermophilic bacterium, Moorella* sp. *HUC22-1*. Biotechnology Letters Volume 26, Number 20 (2004), 1607-1612 and Abrini et al. *Clostridium autoethanogenum*, sp. nov., *an anaerobic bacterium that produces ethanol from carbon monoxide*. Archives of Microbiology Volume 161, Number 4 (1994), 345-351.

Process step A) is preferably carried out under anaerobic conditions.

In process step B) of the process according to the invention, the acetate and/or ethanol formed in process step A), in particular acetate, is separated off from the first microorganism.

In the simplest case, the microorganisms are removed for example by known methods such as sedimentation, centrifugation or filtration as solid from the medium comprising the acetate and/or ethanol, in particular acetate, and optionally the remaining liquid phase is passed directly to process step C). The direct introduction has the advantage that any media constituents additionally still present from process step A), such as, for example, vitamins, trace elements or inducers, are likewise available to the second microorganism in process step C), and is therefore preferred. In this connection, it may be advantageous and therefore preferred to increase the concentration of the acetate and/or ethanol, in particular acetate, prior to introduction to process step C), for example by removing at least parts of the water present. Similarly, the acetate itself can be removed from the microorganisms in process step A) by means of extraction, in particular by means of in situ extraction. Suitable extraction processes are known to the person skilled in the art, thus for example from EP2294206, WO2000014052, U.S. Pat. No. 4,405,717, from Katikaneni et al. *Purification of Fermentation-Derived Acetic Acid By Liquid-Liquid Extraction and Esterification*. Ind. Eng. Chem. Res. 2002, 41, 2745-2752, and from Huh et al. *Selective extraction of acetic acid from the fermentation broth produced by Mannheimia succiniciproducens*. Biotechnol Lett. 2004 October; 26(20):1581-4.

Suitable extractants are described for example under point A *The modified solvent and solvent/co-solvent mixture* on pages 8 to 17 of WO2000014052.

In the case of a separation of the acetate by extraction, extractants preferably present are in particular alkylamines or low-boiling solvent such as MTBE or ethyl acetate, where the alkylamines are preferably those with at least 16 carbon atoms, preferably trialkylamines and particularly preferably trialkylamines selected from the group comprising trihexylamine, trioctylamine, tridecylamine, tricaprylamine, tridodecylamine. These extractants comprising trialkylamines are preferably used in conjunction with an in situ extraction in process step B). This has the technical effect that the first microorganism is not damaged and the additional advantage that process step B) can be carried out in a counterflow process, which is additionally preferred.

In particular, the extractant used in process step B) is a mixture of trioctylamine and 2-ethyl-1-hexanol, these preferably being used in identical amounts.

For detailed process instructions, reference may be made to EP2294206 and process steps A) and B) described therein.

In process step C), the acetate and/or ethanol, in particular acetate, is reacted with a second microorganism to give a hydrocarbon substituted with at least one group containing at least one oxygen atom.

The hydrocarbon substituted with at least one group containing at least one oxygen atom is preferably carboxylic acids, dicarboxylic acids, hydroxycarboxylic acids, carboxylic acid esters, hydroxycarboxylic acid esters, alcohols, aldehydes, ketones, which have in particular 4 to 32, preferably 6 to 20, particularly preferably 8 to 12, carbon atoms. Particular preference is given to carboxylic acids, hydroxycarboxylic acids and carboxylic acid esters.

The second microorganism is preferably yeasts or bacteria.

The second microorganism is preferably a genetically modified strain which has been genetically optimized in particular as regards the yield of the hydrocarbon substituted with at least one group containing at least one oxygen atom.

The person skilled in the art knows from the prior art second microorganisms suitable for the particular target molecule and the process conditions to be applied.

Thus,

WO2011127409, WO2009111672 and WO2010062480 describe suitable second microorganisms and processes for the preparation of fatty alcohols, WO2012017083 for the preparation of fatty acid ethyl esters, WO2011157848, WO2011059745, WO 2009140695, WO2007106903 and WO2009124694 for the preparation of fatty acids, WO2010126891 for the preparation of alcohols, fatty acids and fatty acid esters, WO2010118410, WO2010021711 and WO2010022090 for the preparation of fatty acid esters, WO2010042664 and WO 2009140695 for the preparation of fatty acid aldehydes, WO2012038390, WO2007077568 and WO2011153317 for the preparation of dicarboxylic acids and WO2011008232, WO 2009156214, WO2007141208, WO2004003213, GB2473755 and EP11191923.9 for the preparation of hydroxycarboxylic acids.

In a preferred alternative of the process according to the invention, the hydrocarbon substituted with at least one group containing at least one oxygen atom is fatty acids, in particular linear, saturated fatty acids having 4 to 32, preferably 6 to 20, particularly preferably 8 to 12, carbon atoms. In this connection, the second microorganism is in particular a microorganism which has an increased activity of at least one thioesterase compared to its wild type. The term "an increased activity compared to its wild type" is to be understood as meaning that the microorganism has been genetically modified such that it has this increased activity. Preferably, this is understood as meaning an overexpression of a thioesterase or an expression of an exogenous thioesterase. Thioesterases preferred in this connection are selected from acyl-ACP-thioesterases, preferably EC 3.1.2.14 or EC 3.1.2.22 or acyl-CoA-thioesterases, preferably EC 3.1.2.2, EC 3.1.2.18, EC 3.1.2.19, EC 3.1.2.20 or EC 3.1.2.22. Preferred second microorganisms which are used in the alternative according to the invention are disclosed in WO2010118410, WO2010075483, WO2008119082 and WO2007136762, reference being expressly made to the disclosure content of these documents as regards these microorganisms and as regards these thioesterases.

In a particularly preferred embodiment of the process according to the invention, the fatty acid is octanoic acid and/or decanoic acid and the thioesterase is the gene product of fatB2 from *Cuphea hookeriana*.

In a preferred alternative of the process according to the invention, the hydrocarbon substituted with at least one group containing at least one oxygen atom is hydroxycarboxylic acids, in particular omega-hydroxycarboxylic acids or hydroxyisobutyric acids, in particular 3-hydroxyisobutyric acid. In this connection relating to hydroxyisobutyric acids, the second microorganism is in particular microorganisms which are disclosed in WO2009156214, WO2007141208, WO2009135074 and EP11191923.9, reference being expressly made to the disclosure content of these documents as regards this. In this connection relating to omega-hydroxycarboxylic acid, the second microorganism is in particular microorganisms which are disclosed in WO2011008232, reference being made expressly to the disclosure content of this document as regards this.

It is preferred according to the invention that carbon dioxide produced in process step C) is returned to the process in process step A) and is thus available as a carbon source. This has the technical effect that the carbon yield is 100%.

The examples listed below illustrate the present invention by way of example, without any intention of restricting the invention, the scope of application of which is apparent from the entirety of the description and the claims, to the embodiments specified in the examples.

EXAMPLES

Example 1: Process Step A) Acetate and Ethanol Formation

A live culture of *Clostridium carboxidivorans* DSMZ 15243 was charged to a 1 l anaerobic bottle in 200 ml of modified PETC medium as per Hurst consisting of 1 g of yeast extract, 19 g of MES, 30 ml of mineral salt solution, 10 ml of trace element solution, 10 ml of vitamin solution in 1 l of dd water. The pH was adjusted to a pH of 5.9 with 0.5 M NaOH. The mineral salt solution consists of 80 g of sodium chloride, 100 g of ammonium chloride, 10 g of potassium chloride, 10 g of potassium monophosphate, 20 g of magnesium sulphate, 4 g of calcium chloride per litre. The vitamin solution consists of 0.01 g of pyridoxine, 0.005 g of thiamine, 0.005 g of riboflavin, 0.005 g of calcium pantothenate, 0.005 g of thioctic acid, 0.005 g of (para)aminobenzoic acid, 0.005 g of nicotinic acid, 0.005 g of vitamin B12, 0.002 g of biotin, 0.002 g of folic acid, 0.01 g of MESNA per litre. The trace element solution consists of 2 g of nitriloacetic acid, 1 g of manganese sulphate, 0.8 g of iron ammonium sulphate, 0.2 g of cobalt chloride, 0.2 g of zinc sulphate, 0.02 g of copper(II) chloride, 0.02 g of nickel chloride, 0.02 g of sodium molybdate, 0.02 g of sodium selenate, 0.02 g of sodium tungstate per litre.

The medium was boiled for 20 min and then gassed with pure nitrogen for 20 min. It was then autoclaved for 20 minutes at 121° C. After cooling, the medium was charged 3× with a gas mixture of 50% CO, 45% H2 and 5% $CO_2$ to a superatmospheric pressure of 1 bar. The pressure was then adjusted to superatmospheric pressure of 0.8 bar. Directly prior to inoculation, 1.5 ml of an in each case 4% strength solution of sodium sulphite/cysteine hydrochloride were added as reducing agent under sterile, anaerobic conditions.

The culture was cultivated at 37° C. with 100 rpm (5 cm eccentricity). In each case after 72 hours, the culture was transferred by inoculation to a new medium.

The inoculum for the product preparation was removed from such a 48 h-old culture.

For this purpose, a 2 l stirred vessel, Labfos 2 from Infors HT was filled with 900 ml of the above-described modified PETC medium—excluding MESNA—without the vitamin solution and gassed with nitrogen for 20 minutes. The vessel was then autoclaved at 121° C. for 20 minutes.

The vitamin solution was then added under sterile anaerobic conditions.

The pH was regulated at 5.9 during the entire fermentation with 0.5 M NaOH and 0.5 M HCl.

The gas mixture was adjusted to 80% CO and 20% $CO_2$ using a WMR 4000 gas mixing station from Westphal Mess- and Regeltechnik. Gassing was carried out constantly at 5 l/h.

The stirrer speed was set at a constant 400 rpm, which corresponds to a power input of 0.2 W/l.

Directly prior to the inoculation, 7.5 ml of an in each case 4% strength solution of sodium sulphite/cysteine hydrochloride were added as reducing agent under sterile anaerobic conditions.

The inoculum was 10% and was likewise added under sterile anaerobic conditions 30 minutes after the start of the gasification. The starting $OD_{600}$ was 0.055.

Via a riser tube, 3 ml of sample were drawn off using a syringe after 0/14.4/16.8/20.8/24.2/38.7 h.

The concentration of acetic acid, ethanol, butyric acid and butanol was determined via high performance liquid chromatography (HPLC). The column Aminex HPX-87H was used as the stationary phase. The eluent used was 5 mM sulphuric acid at a constant flow rate of 0.6 ml/min. The temperature of the column was 40° C. Detection of ethanol and butanol was carried out by means of refractive index detector, and acetic acid and butyric acid were detected using a diode array detector at a wavelength of 210 nm. The material concentrations were determined via the peak area by reference to straight calibration lines of defined concentrations.

After 38.7 hours, 0 mM butanol, 1.42 mM butyrate, 3.33 mM ethanol and 54.26 mM acetate were measured. This corresponds to an acetate fraction of 91.95%.

Example 2: Process Step B) Acetate Separation

After separating off the cells, the pH of the fermentation broth was reduced to a pH below 3.0 by adding acetic acid. A tri-n-octylamine solution in 1-octanol in the ratio 1:1 was then added to the fermentation broth and mixed at a stirrer speed of at least 1000 rpm at 25° C. for up to 2 hours with the fermentation broth. Subsequent phase separation was carried out by centrifugation.

The acetic acid was then distilled from the organic phase at 120° C. and a superatmospheric pressure of 500 mbar. The acetic acid content of the distillate was determined by HPLC and the solution was used in the corresponding concentration in the further fermentation (cf. Examples 3 and 4 and 6).

Example 3: Reaction of Acetate to Give C8 and C10 Fatty Acids in Recombinant *E. coli*

The strain *E. coli* JW5020-1 (ΔfadE), available from Yale CGSC, The Coli Genetic Stock Center, was streaked using an inoculation needle from a cryoculture onto an LB agar plate consisting of 5 g of yeast extract, 10 g of peptone, 0.5 g of sodium chloride and 15 g of agar-agar pH 7. The strain *E. coli* JW5020-1 (ΔfadE) pJ294 [Ptac-ChFATB2_optEc] was streaked using an inoculation needle from a cryoculture onto an LB plate which additionally comprises 100 mg/ml ampicillin. The plates were incubated overnight at 37° C.

The strain *E. coli* JW5020-1 (ΔfadE) pJ294 [Ptac-ChFATB2_optEc] is transformed with an expression vector for the gene fatB2 from *Cuphea hookeriana*. To produce the aforementioned vector, this gene was codon-optimized for the expression in *Escherichia coli*. The gene was synthesized together with a tac promoter and at the same time a restriction site upstream of the promoter and a restriction site downstream of the terminator were inserted. The synthesized DNA fragment $P_{tac}$-ChFatB2 (SEQ ID NO. 1). was digested with the restriction endonucleases BamHI and NotI and ligated into the correspondingly cleaved vector pJ294 (DNA2.0 Inc., Menlo Park, Calif., USA). The finished *E. coli* expression vector was referred to as pJ294[Ptac-ChFATB2_optEc] (SEQ ID NO. 2).

Preculture 1: Both cultures were in each case transferred by inoculation in 10 ml of M9, mod-G liquid medium into 100 ml shake flasks with chicanes. The M9 mod-G medium is composed of 2.6 g/l $(NH_4)_2SO_4$, 0.49 g/l $MgSO_4 + 7H_2O$, 20 g/l glucose, 1 ml/l trace elements US3 dissolved in 800 ml M9 buffer and 150 ml $ddH_2O$. The M9 buffer consists of 6.79 g/l $Na_2HPO_2 + 2H_2O$, 3 g/l $KH_2PO_4$, 0.5 g/l NaCl, 2 g/l $NH_4Cl$ dissolved in 800 ml $ddH_2O$. For the plasmid-carrying strain, 100 μg/ml ampicillin were added to the medium.

An inoculation needle was used in each case to transfer a full loop of cell material from the plates to the corresponding liquid media.

The cultures were incubated at 37° C. and 200 rpm overnight.

After 20 hours, the OD was:

| | |
|---|---|
| *E. coli* JW5020-1 (ΔfadE) | 10.6 |
| *E. coli* JW5020-1 (ΔfadE) pJ294[Ptac-ChFATB2_optEc] | 12.8. |

Preculture 2

0.5 ml from preculture 1 were transferred by inoculation in 20 ml of M9, mod-G into 100 ml shake flasks with chicanes. The M9, mod-G medium is composed of 2.6 g/l $(NH_4)_2SO_4$, 0.49 g/l $MgSO_4 + 7H_2O$, 60 mM sodium acetate (from Example 2), 1 ml/l trace elements US3 dissolved in 800 ml M9 buffer and 170 ml $ddH_2O$. For the culture of the plasmid-carrying strain, 100 μg/ml of ampicillin were added.

The cultures were incubated overnight at 37° C. and 200 rpm.

The OD of preculture 2 was

| | |
|---|---|
| *E. coli* JW5020-1 (ΔfadE)/acetate | 2.5 |
| *E. coli* JW5020-1 (ΔfadE) pJ294[Ptac-ChFATB2_optEc]/acetate | 1.75 |

100 ml of modified M9 liquid medium with 60 mM acetate per strain in 1000 ml shake flasks with chicanes were inoculated with the preculture such that an OD of 0.2 was obtained.

The culture was incubated at 37° C. and 225 rpm.

At an $OD_{600}$ of about 0.5, induction was carried out with 1 mM IPTG from a stock solution of 1M IPTG.

For sampling, in each case 4 ml of cell suspension were removed under sterile conditions, the OD was determined and the remaining suspension was stored at −80° C. in 15 ml falcon tubes until the samples were worked up.

Quantification of fatty acids was carried out following derivatization as fatty acid methyl esters by means of gas chromatography. 50 μl of heptadecanoic acid (10 g/l dissolved in ethanol) were added as internal reference substance to the samples consisting of 2 ml of culture broth, following the addition of 1 ml of acetone and 2 ml of water. The samples were acidified with 200 μl of acetic acid and admixed with 10 ml of a 1:1 (v/v) chloroform/methanol mixture. The samples were thoroughly mixed for at least 1 min. The chloroform phase was then removed and evaporated. The dry residue was taken up in 1 ml of 1.25 M methanolic hydrochloric acid and incubated overnight at 50° C. to esterify the fatty acids present. The reaction was stopped by adding 5 ml of saturated sodium carbonate solution (all substances Sigma-Aldrich, Steinheim). The fatty acid methyl esters were extracted by adding 1 ml of n-heptane and vigorously mixing for 15 seconds. The heptane phase is measured by means of gas chromatography. For the separation of fatty acid methyl esters, the capillary column SP™-2560 with the dimensions 100 m×0.25 mm and a film thickness of 0.2 μm (Supelco, Sigma-Aldrich, Steinheim) was used as the stationary phase. The carrier gas used was helium. The separation was carried out over the course of 45 min at an injector temperature of 260° C., detector temperature of 260° C. and column temperature of 140° C. at the start, held for 5 min and increased to 240° C. at a rate of 4° C./min and held for 15 min. The injection volume is 1 μl, the splitting rate 1:20 and the throughput of the carrier gas 1 ml/min. Detection was carried out by means of flame ionization detector (GC Perkin Elmer Clarus 500, Perkin Elmer, Rodgau). Heptadecanoic acid (Sigma-Aldrich, Steinheim) was used as internal reference substance for quantifying the fatty acid methyl ester. The reference substances C8:0-Me caprylic acid methyl ester, C10:0-Me capric acid methyl ester, C12:0-Me lauric acid methyl ester, C14:0-Me myristic acid methyl ester, C16:0-Me palmitic acid methyl ester, C16:1-Me palmitoleic acid methyl ester, C18:0-Me stearic acid methyl ester, C18:1-Me oleic acid methyl ester (GLC Standard Mix GLC-20 1892-1AMP, GLC-30 1893-1AMP, GLC-50 1894-1AMP, Sigma-Aldrich, Steinheim) were used for the calibration. The determination limits for all fatty acid methyl esters are at a concentration of 10 mg/l.

Figure 1:
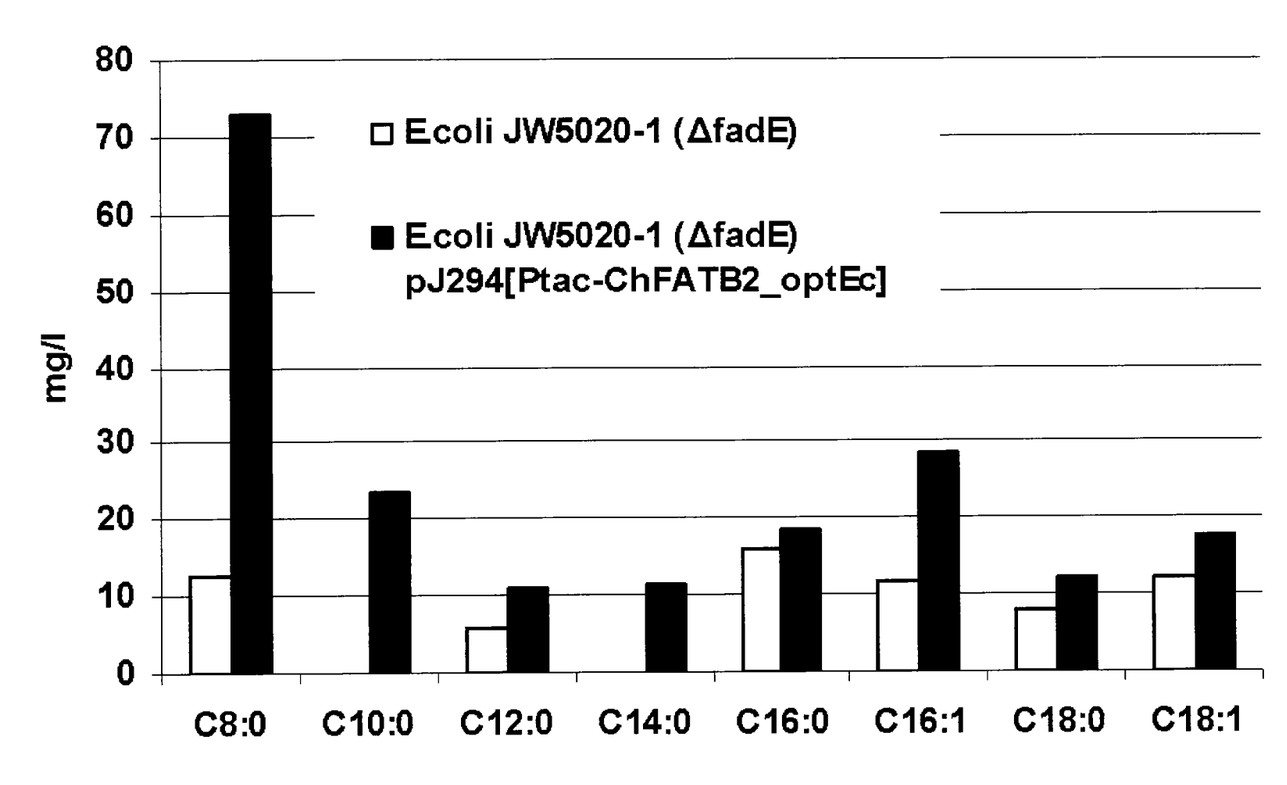
FIG. 1: Fatty acid production in *E. coli* from acetate prepared microbially from synthesis gas

The distribution of the fatty acid concentrations for *E. coli* JW5020-1 (ΔfadE) pJ294[Ptac-ChFATB2_optEc] after 96 hours appears standardized to an OD of 1 as shown in FIG. 1.

Example 4: Reaction of Acetate to Give 3-Hydroxyisobutyric Acid (3-HIB) with *Yarrowia lipolytica* H222-41 Δ3HIBDH (ura)-8

According to Example 1, point 1 to 3 of EP 11191923.9, a *Y. lipolytica* cell H222-41 with attenuated activity of the 3-hydroxyisobutyric acid dehydrogenase was synthesized; this cell is hereinbelow called H222-41 Δ3HIBDH (ura)-8.

H222-41 Δ3HIBDH (ura)-8 was cultivated compared with the corresponding wild type H222-41 (ura)-8.

Cultivation

Both strains were streaked using an inoculation needle under sterile conditions from cryocultures on YEPD agar plates. The YEPD agar plates consist of 10 g of glucose, 10 g of yeast extract, 20 g of peptone and 15 g of agar-agar. The pH is 5.4. Incubation was carried out for 80 hours at 25° C.

Preculture (Biomass Production)

Six 1000 ml shake flasks without chicanes were filled with 100 ml of YEPD liquid medium consisting of glucose, 10 g of yeast extract, 20 g of peptone pH 5.4. Three drops of Delmex antifoam were added to each shake flask.

Per strain, for each three shake flasks, in each case two full loops of cell material were transferred by inoculation under sterile conditions from the corresponding YEPD agar plates using an inoculation needle. Incubation of the shake flasks was carried out for 20 hours at 28° C. and 180 rpm (amplitude 2.5 cm).

Preparation of the Inoculum for the Acetate Culture

After 20 hours, the 3 shake flasks with *Y. lipolytica* H222-41 Δ3HIBDH (ura)-8 and *Y. lipolytica* H222-41 (ura)-8 were combined. The glucose content was determined using the Bioanalytical System YSI 7100 multiparameter from KREIENBAUM Wissenschaftiche Meßsysteme e.K. as 0 g/l. The broths were divided in 50 ml falcon tubes and centrifuged for 10 minutes at 5600 rpm. The supernatant was discarded and the pellets were resuspended in 0.9% strength NaCl solution and centrifuged again for 10 minutes at 5600 rpm. This operation was repeated 2 more times in order to remove possible residual sugars. Then, the pellets were resuspended in each case in 15 ml of acetate medium, the cultures were combined according to strains and topped up with acetate medium to 50 ml in each case.

The acetate medium according to van Uden has the following composition:

Base Medium 5 g/l (NH4)2SO4, 5 g/l KH2PO4, 0.5 g/l MgSO$_4$×7 H2O, 0.15 g/l CaCl$_2$×2 H$_2$O, 4 g/l Na acetate (from Example 2), 5 ml/l vitamin solution, 5 ml/l biotin solution, 5 ml/l trace element solution A, 5 ml/l trace element solution B.

Vitamin Solution 80 mg/100 ml Ca pantothenate, 200 mg/100 ml myoinositol, 160 mg/100 ml nicotinic acid, 160 mg/100 ml pyridoxin HCl, 16 mg/100 ml thiamine HCl.

Biotin Solution

Biotin 8 mg/l

Trace Element Solution A 100 mg/100 ml H$_3$BO$_3$, 20 mg/100 ml KI, 40 mg/100 ml NaMoO$_4$×2 H$_2$O Trace Element Solution B 8 mg/100 ml CuSO$_4$×5 H$_2$O, 40 mg/100 ml FeCl$_5$×6 H$_2$O, 80 mg/100 ml MnSO$_4$×4 H$_2$O, ZnSO$_4$×7 H$_2$O 0.001 N HCl.

The solid constituents of the base medium were dissolved in 700 ml of ddH$_2$O, the pH was adjusted to 5.4 and the medium was autoclaved. The solutions were sterile-filtered and added to the base medium after cooling, the total medium was then topped up to 1000 ml with sterile ddH$_2$O.

Conditioning the Fermenter

Four 800 ml sterile fermenters of a parallel fermentation system from DASGIP were charged with 175 ml of acetate medium. The process conditions were adjusted to 30 pO$_2$ [%], 14 sl/h airflow, 400-1500 rpm stirrer speed, 28° C. temperature, and pH 5.4. The pH was regulated with 0.5% H$_2$SO$_4$ of 25% acetic acid and 12.5% NH$_4$OH. The feed used was a 14% strength Na acetate solution pH 5.4.

Production of 3-HIB

In each case two fermenters were inoculated with 25 ml of inoculum *Y. lipolytica* H222-41 Δ3HIBDH (ura)-8 and *Y. lipolytica* H222-41 (ura)-8.

Sampling was carried out 0, 3, 5, 21, 30 and 46 hours after inoculation. For all of the samples, the OD600 and the acetate content was determined with an Analytical Test Kit from R-Biopharm. The feed was adapted to the acetate consumption.

For the samples at 0 and 46 hours, additionally an NMR determination with D2O as solvent and a water suppression of acetate and 3HIB was carried out.

Result

The OD increases within the experimental period from on average 10 to on average 45.

The acetate content at the start was on average 2250 mg/kg, and at the end of the fermentation 32 mg/l.

The 3HIB content at the start of the fermentation is 0 mg/l both for *Y. lipolytica* H222-41 Δ3HIBDH (ura)-8 and *Y. lipolytica* H222-41 (ura)-8.

After 46 hours, 0 mg/kg are measured for the wild type *Y. lipolytica* H222-41 (ura)-8.

The strain *Y. lipolytica* H222-41 Δ3HIBDH (ura)-8 with the knock-out of the 3-HIB dehydrogenase has produced on average 18 mg/kg 3HIB.

Example 5: Process Step B) Ethanol Separation

Ethanol was separated off in the form of an aqueous concentrate by direct distillation of the fermentation broth from Example 1.

Example 6: Reaction of Acetate and Ethanol to Give Hexanoic Acid and Hexanoic Acid Ethyl Ester with the Anaerobic Bacterium *Clostridium kluyveri*

For the cultivation, pressure-resistant glass bottles which can be sealed in an air-tight manner using a butyl rubber stopper were used. All of the cultivation steps were carried out under anaerobic conditions. The bottles were autoclaved for 20 min at 121° C. in order to ensure sterility.

For the cultures, four pressure-resistant glass bottles (volume 500 ml) were charged with 200 ml of anaerobic medium which is recommended by the DSMZ as medium 52 for *C. kluyveri*. The required acetate and ethanol was used from Examples 2 and 5. The cultures were then inoculated with in each case 10 ml of a culture of *C. kluyveri*. The cultures were in each case sealed with a butyl rubber stopper and incubated for 116.25 h at 35°. Samples were taken at the start and end of the cultivation. These were analysed as to optical density and various analytes by means of NMR. Since hexanoic acid and hexanoic acid ethyl ester can be ascertained by means of NMR only as cumulative parameter, confirmation of the presence of both individual substances in the end samples was carried out by means of GC/MS analysis.

Over the cultivation time, a decrease in the case of acetate from 5.4 g/l to 1.4 g/l and in the case of ethanol from 14.2 g/l to 5.8 g/l was found on average over four replicates. At the same time, a formation of butyric acid was found; here, the value increased from 0.13 g/l to 2.5 g/l, and so too was a formation of hexanoic acid/hexanoic acid ethyl ester; here, the value increased in total from 0.05 g/l to 7.6 g/l.

The invention claimed is:

1. A process for preparing a hydrocarbon substituted with a group comprising an oxygen atom, the process comprising:
   A) reacting a carbon source consisting of at least one of $CO_2$ and CO with a first microorganism such that at least one of acetate and ethanol is produced from the at least one of $CO_2$ and CO, where the first microorganism is an acetogenic microorganism;
   B) separating the at least one of acetate and ethanol from the first microorganism;

C) reacting the at least one of acetate and ethanol separated in B) with a second microorganism such that the hydrocarbon substituted with a group comprising an oxygen atom is produced from the at least one of acetate and ethanol; and optionally D) purifying the hydrocarbon substituted with a group comprising an oxygen atom, wherein a sugar is not used in the reacting in C), and the hydrocarbon substituted with a group comprising an oxygen atom produced in C) is selected from the group consisting of a carboxylic acid having 8 to 32 carbon atoms, a dicarboxylic acid, a hydroxycarboxylic acid, a carboxylic acid ester, a hydroxycarboxylic acid ester, an alcohol having 8 to 32 carbon atoms, an aldehyde, and a ketone.

2. The process according to claim 1, wherein the first microorganism is at least one selected from the group consisting of Clostridium autothenogenum DSMZ 19630, Clostridium ragsdahlei ATCC no. BAA-622, Clostridium autoethanogenum, Moorella sp HUC22-1, Moorella thermoaceticum, Moorella thermoautotrophica, Rumicoccus productus, Acetoanaerobum, Oxobacter pfennigii, Methanosarcina barkeri, Methanosarcina acetivorans, Carboxydothermus, Desulphotomaculum kutznetsovii, Pyrococcus, Peptostreptococcus, Butyribacterium methylotrophicum ATCC 33266, Clostridium formicoaceticum, Clostridium butyricum, Lactobacillus delbrukii, Propionibacterium acidoprprionici, Proprionispera arboris, Anaerobiersipirillum succiniproducens, Bacterioides amylophilus, Becterioides ruminicola, Thermoanaerobacter kivui, Acetobacterium woodii, Acetoanaerobium notera, Clostridium aceticum, Butyribacterium methylotrophicum, Moorella thermoacetica, Eubacterium limosum, Peptostreptococcus productus, Clostridium ljungdahlii, Clostridium ATCC 29797 and Clostridium carboxidivorans.

3. The process according to claim 1, wherein the separating in B) comprises removing the first microorganism from a medium comprising the at least one of acetate and ethanol by sedimentation, centrifugation or filtration.

4. The process according to claim 1, wherein the separating in B) comprises removing the acetate by extraction, with an extractant.

5. The process according to claim 4, wherein the extractant comprises at least one alkylamine selected from the group consisting of trihexylamine, trioctylamine, tridecylamine, tricaprylamine and tridodecylamine.

6. The process according to claim 1, wherein the hydrocarbon substituted with a group comprising an oxygen atom produced in C) comprises a fatty acid, and the second microorganism has an increased activity of a thioesterase compared to its wild type.

7. The process according to claim 1, wherein the hydrocarbon substituted with a group comprising an oxygen atom produced in C) comprises a hydroxycarboxylic acid.

8. The process according to claim 1, wherein the reacting in C) yields carbon dioxide, which is returned to the reacting in A) as the carbon source.

9. The process according to claim 1, wherein the hydrocarbon substituted with a group comprising an oxygen atom produced in C) comprises an omega-hydroxycarboxylic acid, a hydroxyisobutyric acid, or both.

10. The process according to claim 1, wherein the hydrocarbon substituted with a group comprising an oxygen atom produced in C) has 8 to 12 carbon atoms and is selected from the group consisting of a carboxylic acid, a dicarboxylic acid, a hydroxycarboxylic acid, a carboxylic acid ester, a hydroxycarboxylic acid ester, an alcohol, an aldehyde, and a ketone.

11. The process according to claim 1, wherein the hydrocarbon substituted with a group comprising an oxygen atom produced in C) has 8 to 12 carbon atoms and is selected from the group consisting of a carboxylic acid, a hydroxycarboxylic acid, and a carboxylic acid ester.

12. The process according to claim 1, wherein the at least one of acetate and ethanol comprises acetate.

13. The process according to claim 1, wherein the at least one of acetate and ethanol comprises acetate and ethanol.

14. The process according to claim 1, wherein, in the reacting in C), a carbon source reacted with the second microorganism consists of the at least one of acetate and ethanol.

15. The process according to claim 1, wherein the carbon source in A) comprises at least 90% by weight of $CO_2$.

16. The process according to claim 1, wherein the hydrocarbon substituted with a group comprising an oxygen atom produced in C) has 8 to 32 carbon atoms and is selected from the group consisting of a carboxylic acid, a dicarboxylic acid, a hydroxycarboxylic acid, a carboxylic acid ester, a hydroxycarboxylic acid ester, an alcohol, an aldehyde, and a ketone.

17. The process according to claim 1, wherein the second microorganism is yeast or a bacterium.

18. The process according to claim 1, wherein the hydrocarbon substituted with a group comprising an oxygen atom produced in C) is octanoic acid, decanoic acid, or both.

19. The process according to claim 6, wherein the thioesterase is encoded by a fatB2 gene from Cuphea hookeriana.

20. A process for preparing octanoic acid, decanoic acid, or both, the process comprising:

A) reacting a carbon source consisting of at least one of $CO_2$ and CO with a first microorganism such that at least one of acetate and ethanol is produced from the at least one of $CO_2$ and CO;

B) separating the at least one of acetate and ethanol from the first microorganism;

C) reacting the at least one of acetate and ethanol separated in B) with a second microorganism such that octanoic acid, decanoic acid, or both is produced from the at least one of acetate and ethanol; and optionally D) purifying the octanoic acid, decanoic acid, or both produced in C), wherein a sugar is not used in the reacting in C).

* * * * *